United States Patent [19]

Weber et al.

[11] Patent Number: 5,011,834

[45] Date of Patent: Apr. 30, 1991

[54] PCP RECEPTOR LIGANDS AND THE USE THEREOF

[75] Inventors: Eckard Weber, Portland; John F. W. Keana; Peter Barmettler, both of Eugene, all of Oreg.

[73] Assignee: State of Oregon, acting by and through the Oregon State Board of Higher Education, acting for and on behalf of the Oregon Health Sciences University and the University of Oregon, Portland, Oreg.

[21] Appl. No.: 337,858

[22] Filed: Apr. 14, 1989

[51] Int. Cl.$^5$ .............................................. A61K 31/55
[52] U.S. Cl. .................................................... 514/212
[58] Field of Search .......................................... 514/212

[56] References Cited

U.S. PATENT DOCUMENTS

| | | | |
|---|---|---|---|
| 3,509,158 | 4/1970 | Dobson et al. | 260/287 |
| 3,542,787 | 11/1970 | Dobson et al. | 260/286 |
| 3,597,433 | 8/1971 | Dobson et al. | 260/286 |
| 3,641,038 | 2/1972 | Davis et al. | 260/289 |
| 3,716,541 | 2/1973 | Dobson et al. | 260/286 |
| 3,717,641 | 2/1973 | Kocsis et al. | 260/286 |
| 3,812,119 | 5/1974 | Walker et al. | 260/247 |
| 3,892,756 | 7/1975 | Nedelec et al. | 260/289 |
| 4,052,508 | 10/1977 | Anderson et al. | 424/258 |
| 4,064,139 | 12/1977 | Anderson et al. | 260/313.1 |
| 4,148,898 | 4/1979 | Koch et al. | 424/256 |
| 4,232,158 | 11/1980 | Shepard et al. | 546/72 |
| 4,374,838 | 2/1983 | Anderson et al. | 424/256 |
| 4,399,141 | 2/1983 | Anderson et al. | 424/256 |
| 4,465,677 | 8/1984 | De Marinis et al. | 424/244 |
| 4,762,828 | 8/1988 | Georgiev et al. | 514/214 |
| 4,789,673 | 12/1988 | Donatsch et al. | 514/214 |

FOREIGN PATENT DOCUMENTS

0230370  1/1987  European Pat. Off. ............. 37/435

*Primary Examiner*—Stanley J. Friedman
*Assistant Examiner*—Diane Gardner
*Attorney, Agent, or Firm*—Sterne, Kessler, Goldstein & Fox

[57] ABSTRACT

The invention relates to methods for the treatment or prevention of neuronal loss in ischemia, hypoxia, hypoglycemia, brain and spinal cord trauma as well as for treatment of Alzheimer's disease, amyotrophic lateral sclerosis, Huntington's disease, and Down's Syndrome by administering a pharmaceutical composition comprising an effective amount of 10,5-(iminomethano)-10,11-dihydro-5H-dibenzo[a,d]cycloheptene (IDDC) or derivatives thereof to an animal.

26 Claims, 2 Drawing Sheets

FIG. 2

PCP RECEPTOR LIGANDS AND THE USE THEREOF

FIELD OF THE INVENTION

The invention is in the field of pharmaceutical compositions which are useful for the prevention and/or treatment of neurodegradation and other neuropathological conditions in animals.

BACKGROUND OF THE INVENTION

The amino acid L-glutamate is widely thought to act as a chemical transmitter substance at excitatory synapses within the central nervous system. Neuronal responses to glutamate are complex and appear to be mediated by at least three different receptor types, i.e., KA, QA and NMDA subtypes, each being named for their relatively specific ligands, i.e., kainic acid, quisqualic acid and N-methyl-D-aspartic acid, respectively.

NMDA receptors are strongly involved in nerve cell death which occurs following brain ischemia or hypoxia. Upon the occurrence of ischemic/hypoxic brain insults such as those which occur during spinal or head trauma, stroke or heart attack, an excessive release of endo. genous glutamate occurs from nerve terminals deprived of the energy supplies needed to retain the neurotransmitter. The excessive amounts of glutamate cause an over-stimulation of NMDA receptors on nearby neurons. Associated with the NMDA receptors is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor plays an important role in neuronal death. See, e.g., Rothman, S. M. and Olney, J. W., *Trends in Neurosci.* 10(7), 299–302 (1987).

Agents which block responses to NMDA receptor activation therefore have potential therapeutic uses in the treatment of neurological disorders and nerve cell death resulting from hypoxia or hypoglycemia or following brain ischemia which occurs during stroke, trauma and heart attack. A number of disorders of the nervous system are associated with neurodegeneration that may be caused by over-activation of NMDA receptors. Antagonists of NMDA receptor-mediated responses have potential therefore for the treatment of such disorders as Alzheimer's disease, Huntington's chorea, amyotrophic lateral sclerosis and Down's Syndrome.

Research on the NMDA receptor-ion channel complex has led to the determination of a receptor site within the ion channel known as the PCP receptor. See Vincent, J. P., Kartalovski, B., Geneste, P., Kamenka, J. M. and Lazdunski, M., *Proc. Natl. Acad. Sci. USA* 76. 4678. 4682 (1979); Zukin, S. R. and Zukin, R. S., *Proc. Natl. Acad. Sci. USA* 76, 5372–5376 (1979); Sonders, M. S., Keana, J. F. W. and Weber, E., *Trends in Neurosci.* 11(1), 37–40 (1988); and Anis, N. A., Berry, S. C., Burton, N. R. and Lodge, D., *Br. J. Pharmacol.* 79, 565–575 (1983). Compounds which bind to the PCP receptor can act as ion channel blockers, thereby interrupting the flow of ions across the cell membrane. In this manner, agents which interact with the PCP receptor act as non-competitive blockers, reducing the agonist action of glutamate at the NMDA receptor.

Known PCP receptor ligands include PCP [angel dust], i.e., phencyclidine, analogues such as 1-[1-(2-thienyl)-cyclohexyl]-piperidine (TCP), benzomorphan (sigma) opiates, dioxolanes and 5-methyl-10, 11-dihydro-5H-dibenzo[a,d]cycloheptene-5,10-imine (i.e. MK-801, see U.S. Pat. No. 4,399,141). See, also, Wong, E. H. F., Kemp, J. A., Priestly, T., Knight, A. R., Woodruff, G. N., and Iversen, L. I., *Proc. Natl. Acad. Sci. USA* 83, 7104–7108 (1986). MK-801 is apparently the most potent selective PCP receptor ligand/NMDA channel blocker known to date.

European Patent Application Publication No. 0230370, Published July 29, 1987, discloses compounds having the Formula(I):

Where $R^1$, $R^2$, $R^3$, and $R^4$ are H, the compound is MK-801. This compound and derivatives thereof are the subject of a patent to Anderson et al., U.S. Pat. No. 4,399,141 (1983).

U.S. Pat. No. 4,374,838 to Anderson et al. (1983) discloses compounds related to MK-801 of the Formula (II):

which are useful as muscle relaxants, antidepressants, anticonvulsants, and in the treatment of mixed anxiety-depression, minimal brain dysfunction, and extrapyramidal disorders.

U.S. Pat. No. 4,064,139 to Anderson et al. (1977) discloses compounds related to MK-801 of Formula (III):

which are useful as minor tranquilizer, anticonvulsants, muscle relaxants, and in the treatment of extrapyramidal disorders such as Parkinson's disease.

U.S. Pat. No. 3,509,158 to Dobson et al. (1970) discloses 10,5- (iminomethane)-10,11-dihydro-5H-dihydro-5H-dibenzo[a,d]-cycloheptene and derivatives of the Formula (IV):

(IV)

wherein Z represents a group selected from the groups consisting of

These compound are reportedly useful as trichomonacidal, anticonvulsants, anti-parasitic, anti-inflammatory and hypotensive agents.

U.S. Pat. No. 4,232,158 to Shepard et al. (1980), discloses 10,11-dihydro-5H-dibenzo[a,d]cyclohepten-5,10-imines and derivatives thereof having the following structural Formula (V):

(V)

These compounds are reported useful as anti-anxiety agents, as muscle relaxants and in the treatment of extrapyramidal disorders such as Parkinson's disease.

U.S. Pat. No. 3,641,038 to Davis et al. (1972), discloses 10,11-dihydro-10,5-(iminomethano)-5H-dibenzo[a,d]-cyclohepten-10-ol derivatives having the Formula (VI):

(VI)

These compounds reportedly possess anti-convulsant activities.

U.S. Pat. No. 3,542,787 to Dobson et al. (1970), discloses 10,11-dihydro-5,10-(iminomethano)-5H-dibenzo[a,d]-cycohepten-13-imine having the Formula (VII):

(VII)

This compound reportedly has hypotensive properties.

U.S. Pat. No. 3,597,433 to Dobson et al. (1971), discloses 10,11-dihydro-5,10-(iminomethano)-5H-dibenzo[a,d]-cycloheptene and its derivatives having the following Formula (VIII):

(VIII)

These compounds reportedly have anticonvulsant activity substantially free from ataxic side-effects.

U.S. Pat. No. 3,716,451 to Dobson et al. (1973) discloses 11-substituted derivatives of 10,11-dihydro-5,10-(iminomethano)-5H-dibenzo[a,d]-cycloheptane having the Formula (IX);

(IX)

The compunds reportedly exhibit central nervous system depressant and anticonvulsants properties without causing ataxia.

U.S. Pat. No. 3,717,641 to Kocsis et al. (1973), discloses 5,6,11,12-tertrahydrodibenzo[a,e]cycloocten-5,11-imine having the Formula (X);

(X)

These compounds reportedly have anti-tussive and musculotropic spasmolytic activities.

U.S. Pat. No. 3,892,756 to Nedelec et al. (1975), discloses 1,10-imino-dibenzo-cycloheptenes having the Formula (XI):

(XI)

These compounds are reportedly useful as stimulants and anticonvulsants.

U.S. Pat. No. 4,009,273 to Nedelec et al. (1977), discloses compounds of the Formula (XII):

(XII)

These compounds are reportedly useful as stimulants and anticonvulsants.

U.S. Pat. No. 4,052,508 to Anderson et al. (1977), discloses dihydroanthracen imines and derivatives thereof having the Formula (XIII):

(XIII)

These compounds are reportedly useful as minor tranquilizers, anticonvulsants, muscle relaxants, and in the treatment of extrapyramidal disorders such as Parkinson's disease.

U.S. Pat. No. 4,064,139 to Anderson et al. (1977), discloses substituted 9,10-dihydroanthracene-9,10-imines having the Formula (XIV):

(XIV)

These compounds are reportedly useful as minor tranquilizers, anticonvulsants, muscle relaxants, and in the treatment of extrapyramidal disorders such as Parkinson's disease.

Despite the development of the above-mentioned derivatives, a need continues to exist for new methods for the treatment or prevention of neuronal loss associated with stroke, ischemia, CNS trauma, and hypoglycemia, as well as for the treatment or prevention of neurodegenerative diseases including Alzheimer's disease, amyotrophic lateral sclerosis, Huntington's disease, and Down's syndrome

SUMMARY OF THE INVENTION

The invention relates to a method of treating or preventing neuronal loss associated with stroke, ischemia, CNS trauma, and hypoglycemia, as well as treating neurodegenerative diseases including Alzheimer's disease, amyotrophic lateral sclerosis, Huntington's disease and Down's syndrome, comprising administering to an animal in need of such treatment a compound of the Formula (XVI):

(XVI)

wherein:

R is hydrogen, $C_2$-$C_6$ acyl, $C_1C_6$ alkyl, aryl, $C_1$-$C_6$ alkoxycarbonyl, $C_7$-$C_{10}$ aralkyl, $C_2$-$C_6$ alkenyl, $C_3$-$C_{15}$ dialkylaminoalkyl, $C_1$-$C_6$ hydroxyalkyl, $C_2$-$C_6$ alkynyl, $C_3$-$C_{15}$ trialkylsilyl, $C_4$-$C_{10}$ alkylcycloalkyl, or $C_3$-$C_6$ cycloalkyl;

$R^1$ is hydrogen, $C_1$-$C_6$ alkyl, $C_2$-$C_6$ alkenyl, $C_7$-$C_{10}$ aralkyl, $C_1$-$C_6$ or $C_3$-$C_{15}$ dialkylaminoalkyl;

X and Y are independently selected from the group consisting of a halogen such as chloro, fluoro, bromo, iodo, $C_1$-$C_6$ alkoxy, $C_2$-$C_6$ dialkoxymethyl, $C_1$-$C_6$ alkyl, cyano, $C_3$-$C_{15}$ dialkylaminoalkyl, carboxy, carboxamido, $C_1$-$C_6$ haloalkyl, $C_1$-$C_6$ haloalkylthio, allyl, aralkyl, $C_3$-$C_6$ cycloalkyl, aroyl, aralkoxy, $C_2$-$C_6$ acyl, aryl, substituted aryl, heteroaryl, substituted heteroaryl, $C_5$-$C_6$ heterocycloalkyl, $C_1$-$C_6$ alkylthio, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, arylthio, $C_1$-$C_6$ haloalkoxy, amino, $C_1$-$C_6$ alkylaminol, $C_2$-$C_{15}$ dialkylamino, hydroxy, carbamoyl, $C_1$-$C_6$ N-alkylcarbamoyl, $C_2$-$C_{15}$ N,N-dialkylcarbamoyl, nitro and $C_2$-$C_{15}$ dialkylsulfamoyl;

Z represents a group selected from wherein $R^2$ is hydrogen, $C_1$-$C_6$ alkyl, $C_2$-$C_6$ alkenyl, aralkyl, $C_4$-$C_{15}$ dialkylaminoalkyl, heteocycloalkyl, $C_214$ $C_6$ acyl, aroyl, or aralkanoyl, and $R^3$ $C_1$-$C_6$ alkyl, $C_2$-$C_6$ alkenyl, phenyl, aralkyl or $C_3$-$C_{15}$ dialkylaminoalkyl; and n is an integer selected from 0 (X or Y is hydrogen, respectively), 1, 2, 3, or 4;

or a pharmaceutically acceptable salt thereof;

wherein said compound exhibits a high binding activity with respect to the PCP receptor in mammalian nerve cells, and is administered in an amount effective to treat or prevent said neuronal loss or to treat said disease.

DESCRIPTION OF THE PREFERRED EMBODIMENTS

The invention relates to a method of treating or preventing neuronal loss associated with stroke, ischemia, CNS trauma, and hypoglycemia, as well as treating neurodegenerative diseases including Alzheimer's disease, amyotrophic lateral sclerosis, Huntington's disease, and Down.s syndrome, comprising administering to an animal, i.e. a human, in need of such treatment a pharmaceutical composition comprising a compound of the Formula (XVI):

(XVI)

wherein:

R is hydrogen, $C_2$–$C_6$ acyl, $C_1$–$C_6$ alkyl, aryl, $C_1$–$C_6$ alkoxycarbonyl, $C_7$–$C_{10}$ aralkyl, $C_2$–$C_6$ alkenyl, $C_3$–$C_{15}$ dialkylaminoalkyl, $C_1$–$C_6$ hydroxyalkyl, $C_2$–$C_6$ alkynyl, $C_3$–$C_{15}$ trialkylsilyl, $C_4$–$C_{10}$ alkylcycloalkyl, or $C_3$–$C_6$ cycloalkyl;

$R^1$ is hydrogen, $C_1$–$C_6$ alkyl, $C_2$–$C_6$ alkenyl, $C_7$–$C_{10}$ aralkyl, $C_1$–$C_6$ alkoxy or $C_3$–$C_{15}$ dialkylaminoalkyl;

X and Y are independently selected from the group consisting of a halogen such as chloro, fluoro, bromo, iodo, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkyl-sulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbomyl, $C_2$–$C_{15}$ N,N-dialkylcarbamoyl, nitro and $C_2$–$C_{15}$ dialkylsulfamoyl;

Z represents a group selected from wherein $R^2$ is hydrogen, $C_1$–$C_6$ alkyl, $C_2$–$C_6$ alkenyl, aralkyl, $C_4$–$C_{15}$ dialkylaminoalkyl, heteocycloalkyl, $C_2$–$C_6$ acyl, aroyl, or aralkanoyl, and $R_3$ is $C_1$–$C_6$ alkyl, $C_2$–$C_6$ alkenyl, phenyl, aralkyl or $C_3$-$C_{15}$ dialkylaminoalkyl; and n is an integer selected from 0 (X or Y is hydrogen, respectively), 1, 2, 3 or 4, or a pharmaceutically acceptable salt thereof;

wherein said compound exhibits a high binding activity with respect to the PCP receptor in mammalian nerve cells, and is administered in an amount effective to treat or prevent said neuronal loss or to treat said disease.

The compounds having Formula (XVI) above may exist in racemic form or in the optically active stereoisomeric form.

Preferably, the compounds of the invention are those of Formula (XVI) wherein R is H, i.e., those having the following structural Formula (XVII):

(XVII)

wherein $R^1$, X, Y, Z and n are as defined above.

Typical $C_1$–$C_6$ alkyl groups include methyl, ethyl, n-propyl, i-propyl, n-butyl, t-butyl, i-butyl, pentyl and hexyl groups.

Typical $C_2$–$C_6$ acyl groups include acetyl, propanoyl, i-propanoyl, butanoyl, s-butanoyl, pentanoyl and hexanoyl groups.

Typical aryl groups include phenyl, naphthyl, phenanthryl and anthracyl groups.

Typical $C_1$–$C_6$ alkoxycarbonyl groups include carbonyl substituted by methoxy, ethoxy, propanoxy, i-propanoxy, n-butanoxy, t-butanoxy, ibutanoxy, pentanoxy, and hexanoxy groups.

Typical aralkyl groups include the above-listed $C_1$–$C_6$ alkyl groups substituted by phenyl, naphthyl, phenanthryl and anthracyl groups.

Typical $C_2$–$C_6$ alkenyl groups include vinyl, allyl, 2-butenyl, 2-pentenyl, and 2-hexenyl groups.

Typical $C_2$–$C_6$ alkynyl groups include acetynyl and propargyl groups.

Typical halo groups include fluorine, chlorine, bromine and iodine.

Typical aroyl groups include carbonyl substituted by phenyl, naphthyl, phenanthryl and anthracyl groups.

Typical aralkanoyl groups include carbonyl substituted by the above-listed aralkyl groups.

Typical aralkoxy groups include the above listed $C_1$–$C_6$ alkoxy groups substituted by phenyl, naphthyl, phenanthyl and anthracyl groups.

Typical substituted aryl groups include the above-listed aryl groups substituted by halo, hydroxy, amino, and the like.

Typical heteroaryl groups include furyl, thienyl, pyrrolyl, thiazolyl, pyridyl, pyrimidinyl, pyrizinyl and oxazolyl groups.

Typical substituted heteroaryl groups include the above-listed heteroaryl groups substituted by halo, $C_1$–$C_6$ alkyl and the like.

Typical $C_5$–$C_6$ heterocycloalkyl groups include tetrahydrofuranyl, tetrahydropyranyl, piperidinyl and pyrrolidinyl groups.

With reference to Formula (XVI), a most preferred compound, wherein X, Y, R and $R^1$ are hydrogen (n is D), is 10,5-(iminomethano)-10,11-dihydro-5H-dibenzo[a,d]cycloheptene (IDDC) having the following Formula (XVIII):

(XVIII)

With reference to Formula (XVI), a second preferred compound wherein X, Y and R are hydrogen (n=0) and $R^1$ is $CH_3$ is 5-methyl-10,5-(iminomethano)-10, 11-dihydro-5H-dibenzo[a,d]cycloheptene (5-methyl-IDDC) having the following Formula (XIX):

(XIX)

With reference to Formula (XVI), a third preferred compound wherein X, Y and $R^1$ are hydrogen (n=0) and R is $CH_3$ is N-methyl-10,5-(iminomethano)-10, 11-dihydro-5H-dibenzo[a,d]cycloheptene (N-methyl-IDDC) having the following Formula (XX):

(XX)

With reference to Formula (XVI), a fourth preferred compound wherein X and Y are hydrogen and R and R$^1$ are CH$_3$ is 5-methyl-N-methyl-10,5-(iminomethano)-10,11-dihydro-5H-dibenzo[a,d]cycloheptene (5-methyl-N-methyl-IDDC) having the following Formula (XXI):

(XXI)

The compounds of the invention exhibit high binding activity with respect to the PCP receptor in mammalian nerve cells. Compounds with especially high binding activity include those represented by Formulae (XVIII)-(XXI), above.

Further, this invention relates to a method of ameliorating the neurotoxic effect induced by glutamate interacting with the NMDA receptor of a nerve cell, comprising the administration, to an animal, e.g., a human being, exhibiting symptoms of or susceptible to such neurotoxic effect, of a compound of the invention which has a high affinity for the PCP receptor of the nerve cell in an amount effective to block the ion channel of the NMDA receptor-ion channel complex. Such neurotoxic effects may be caused by ischemic brain insults which cause excessive release of endogenous glutamate. The pharmaceutical compositions of the invention may be administered prophylactically, for example, before a surgical procedure or other treatment which may be expected to cause reduced blood flow to the brain or spinal cord, thereby, preventing or ameliorating neurodegradation. The pharmaceutical compositions of the invention may also be administered after trauma to, for example, the head or spinal cord to prevent or ameliorate the resulting neurodegeneration which may result therefrom.

A number of disorders of the nervous system are associated with neurodegradation that may be caused by over-activation of NMDA receptors. Therefore, agents which block responses to NMDA receptor activation have therapeutic use in the treatment of neurological disorders and also in the prevention of nerve cell death resulting from hypoxia or hypoglycemia or following brain ischemia which occurs during stroke, trauma and heart attack. Antagonists of NMDA receptormediated responses also are useful for the treatment of such disorders as Alzheimer's disease, Huntington's chorea, amyotrophic lateral sclerosis and Down's Syndrome.

The invention also relates to a method of inhibiting NMDA receptor ion channel-related neurotoxicity comprising administering to an animal a compound of Formula (XVI) which possesses a high affinity for the PCP receptor of a nerve cell, in an amount effective to inhibit the neurotoxicity.

One of ordinary skill in the art may readily determine the activity of a particular compound represented by Formula (XVI) as a non-competitive blocker of NMDA receptor agonist by: (a) determining the binding affinity with respect to the PCP receptor by competitive displacement of tritiated thienylcyclohexylpiperidine ([$^3$H]TCP; see Vignon et al., *Brain Res.* 280:194-197 (1983); Contreras et al; *Neurosci. Lett.* 67:101-106 (1986)); (b) evaluating the ability of compounds to block the passage of ions through ion channels by measurement of electrical current through the channel (Huettner and Bean, *Proc. Natl. Acad. Sci. (USA)* 85:1307-1311 (1988)); (c) in vitro cytotoxicity studies measuring the ability of the compound to prevent nerve cell death caused by exposure to glutamate: and/or (d) determination of in vivo neuroprotective ability using animal models.

Evaluation of the binding activity of organic compounds with respect to the PCP receptor is performed using radioligand binding assays. The compounds are tested to determine their ability to displace tritiated-TCP and tritiated-MK-801 which are used to label PCP receptors. Evaluating the competitive displacement binding data, the preferred compounds are those which exhibit a high affinity (i.e., low IC$_{50}$ value) for the PCP receptors.

Under the binding activity studies, an IC50 value of at most about 1000 nM, preferably at most about 500 nM, indicates a high binding affinity. In the present application, the term 'high affinity" is intended to mean a compound which exhibits an IC$_{50}$ value of at most about 1000 nM.

In the electrophysiological studies the compounds are evaluated with respect to their ability to block the ion channel of the NMDA receptor channel complex and thereby inhibit Ca$^{2+}$ and Na$^+$ ion flow into the nerve cell. Initially, the ion channels are opened by activating the NMDA receptor. Ion flow is determined by measuring the passage of electrical current, i.e., a use-dependant decrease in electrical current indicates blocking of the ion channel due to binding of a ligand at a site within the channel.

A use-dependant block means that as more NMDA receptor-channel complexes are activated by glutamate, blockage of the channels by the non-competitive blocking agent become more effective.

In the cytotoxicity studies, cultured mammalian neurons expressing EAA receptors are exposed in vitro to glutamate and the particular compound under investigation. The survival percentage of cells indicates the ability of the compound to protect against glutamateinduced neuronal death.

In the in vivo neurotoxicity studies, the experimental model of McDonald, D. W., et al., (In: Sigma and Phencyclidine-like Compounds as Molecular Probes in Biology, Ed. Domino, E. F., and Kamenka, J. M., pp. 697-707 (1988), NPP Books, Ann Arbor, Mich.) may be employed. In this model, NMDA injection into one cerebral hemisphere causes injury which resembles the lesion produced by hypoxia-ischemia. The ability of compounds to limit the NMDA-induced lesion is a measure of their neuroprotective properties; since the compounds may be administered intraperitoneally, the model can also provide information about a compound's ability to cross the blood-brain barrier.

In general, the compounds having Formula (XVI) are prepared according to Scheme I shown below, for example, by heating the diaryl derivative having Formula (XXII) with bromoacetaldehyde diethylacetal in a polar aprotic solvent. Polar aprotic solvents which can be used for this purpose include N,N-dimethylformamide (DMF) and dimethylsulfoxide (DMSO). The temperature of the reaction mixture may range from 70° C. to 120° C. The product having the Formula (XXIII) is then treated with an acid such as trifluoromethanesulfonic acid or 70% perchloric acid in a solvent such as chloroform or dichloromethane at ambient temperature to give a compound having the Formula (XXIV). This compound may then be derivatized at the nitrogen atom with a suitable electrophile to give the compound represented by Formula (XVI). For example, the N-methyl derivative may be prepared by reaction of (XXIV) with formaldehyde and sodium borohydride. Alternatively, the nitrogen of Formula (XXIV) may be reacted with an alkyl halide, alkanoyl halide, or other suitable electrophile.

Where X and Y are not hydrogen, the product having Formula (XVI) may be prepared by selecting an appropriately substituted diaryl derivative (XXII) which may be prepared by electrophilic substitution on the phenyl ring(s) according to methods known to those skilled in the art.

Where Z is a carbon atom bearing a hydroxy or an alkoxy substituent, the compounds may be prepared according to U. S. Pat. Nos. 3,509,158, 3,426,015 and 3,361,767, the disclosures of which are incorporated herein by reference.

The 5-substituted of Formula (XVI) may be prepared according to Scheme II shown below, for example, by treatment of the diaryl derivative (XXII) with an alkynyl derivative (XXV) such as 3-bromo-1-propyne in an alcoholic medium containing a base such as potassium carbonate to give the substituted N-propargyl-1,2-diaryl-ethylamine (XXVI). Where Z is a carbon atom bearing a hydroxy group, the hydroxy group may be protected by a suitable hydroxy protecting group such as benzyl and the like. Treatment of (XXVI) with an acid such as trifluoromethanesulfonic acid gives a compound having formula (XXVII). This product may be further derivatized at the nitrogen or hydroxy group (where Z is substituted by alkoxy or acyloxy) by treatment with an appropriate electrophile, as discussed above.

Also included within the scope of the present invention are the optical isomers of the compound having Formula (XVI) The optical isomers may be separated by classical resolution techniques by, for example, formation of a salt of the amino group of Formula (XVI) with an optically active acid. A particularly preferred acid for this purpose is (+)-di-p-toluoyl-0-tartaric acid. The resulting diastereoisomeric salt may then be separated by crystallization, chromatography, or by taking advantage of the differing solubilities of the two diastereoisomeric salts The free base may then be isolated by treatment with a base such as aqueous ammonia and extraction with an organic solvent.

Alternatively, the optical isomers may be prepared by resolution of the diaryl derivative (XXII) For example, 1,2-diphenylethylamine may be resolved by preparation of corresponding diastereoisomeric salt with an optically active acid. A particularly preferred acid for this purpose is L-(+)-tartaric acid. The diastereoisomeric salt may be separated by crystallization followed by isolation of the free base as discussed above. The optically active 1,2-diphenylethylamine may then be carried through the reaction sequence shown in Scheme I or II to give the optically active product having Formula (XVI).

The above synthesis was readily adapted to allow determination of the absolute configuration of (+)-IDDC as follows. (−)-1,2-Diphenyl- ethylamine had already been shown (M. Nakazaki et al., Bull. Soc. Chem. Japan 36:316 (1963)) to have the R-absolute configuration. During the synthesis of (+)-IDDC from (R)(−)-1,2-diphenylethylamine the R-configuration is retained and it becomes C-10 in the IDDC molecule. Therefore the absolute configuration of (+)-IDDC is R at C-10. Owing to the geometric constraints imposed on the molecule by the bicyclic ring structure, the absolute configuration at C-5 in (+)-IDDC must then be S. The full name of (+)-IDDC is therefore (+)-10(R),5(S)-

(iminomethano)-10,11-dihydro-5H-dibenzo[a,d]cycloheptene.

Also included within the scope of the present invention are the non-toxic pharmaceutically acceptable salts of the compounds having Formula (XVI). Acid addition salts are formed by mixing a solution of a compound having Formula (XVI) with a solution of a pharmaceutically acceptable non-toxic acid such as hydrochloric acid, fumaric acid, maleic acid, succinic acid, acetic acid, citric acid, tartaric acid, carbonic acid, phosphoric acid oxalic acid, and the like.

In the method of treatment or prevention of neuronal loss in ischemia, brain and spinal cord trauma, hypoxia, and hypoglycemia, as well as for the treatment of Alzheimer's disease, amyotrophic lateral sclerosis, Huntington,s disease and Down,s Syndrome, the pharmaceutical compositions of the invention may comprise the compound of Formula (XVI) at a unit dose level of about 0.01 to about 500 mg/kg of body weight, or an equivalent amount of the pharmaceutically acceptable salt thereof, on a regimen of 1-4 times per day. When used in a method of treating a disease in which the pathophysiology of the disorder involves NMDA receptor-ion channel related neurotoxicity, the compound having Formula (XVI) may be administered at a unit dosage level of from about 0.01 to about 500 mg/kg of body weight, or an equivalent amount of the pharmaceutically acceptable salt thereof, on a regimen of 1-4 times per day Of course, it is understood that the exact treatment level will depend upon the case history of the animal, e.g., human being, that is treated The precise treatment level can be determined by one of ordinary skill in the art without undue experimentation.

The pharmaceutical compositions of the invention may be administered to any animal which may experience the beneficial effects of the compounds of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes Alternatively, or concurrently, administration may be by the oral route. The dosage administered will be dependent upon the age, health and weight of the recipient, kind of concurrent treatment, if any, frequency of treatment, and the nature of the effect desired.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, are present at a concentration of from about 0.01 to 99 percent, together with the excipient The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above.mentioned starches and also carboxymethylstarch, cross-linked polyvinyl pyrrolidone, agar, or alginic acid or a salt thereof, such as sodium alginate. Auxiliaries are, above all, flow. regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethylcellulose phthalate, are used Dye stuffs or pigments may be added to the tablets or dragee coatings, for example, for identification or in order to characterize combinations of active compound doses Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers In soft capsules, the active compounds are preferably dissolved or suspended in suitable liquids, such as fatty oils, or liquid paraffin In addition, stabilizers may be added.

Possible pharmaceutical preparations which can be used rectally include, for example, suppositories, which consist of a combination of one or more of the active compounds with a suppository base Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Example 1: Synthesis of IDDC

A. Synthesis of N-(2,2-diethoxyethyl)-diphenylethylamine

N-(2,2-diethoxyethyl)-diphenylethylamine was prepared according to the procedure of Takayama, H., *Chem. Lett.* 865 (1978). To a stirred solution of 1,2-diphenylethylamine (3.94 g, 20.0 mmol, Aldrich Co., used as received) in N,N-dimethylformamide (DMF) (10 ml) at 8090° C. was added dropwise over 1 h freshly distilled bromoacetaldehyde diethylacetal (4.50 g, 22.5 mmol, Aldrich Co.). After 13 h, potassium carbonate (2.76 g, 20.0 mmol) was added. After 13 h, the brown mixture was cooled to 25° C, and then the mixture was diluted with 1 N NaOH (200 ml), extracted twice with $CH_2C_{12}$ (total of 100 ml), and dried ($MgS_{04}$). The solvent was evaporated and the residue was distilled to give N-(2,2-diethoxyethyl)-diphenylethylamine (5.29 g, 84%): bp 150-160° C./0.50 mm: $^1$H NMR ($CDCl_3$) ≃1.10 (t, 3), 1.12 (t, 3), 1.70 (bs, 1), 2.50 (dd, 1), 2.58 (dd, 1) 2.91 (dd, 1), 2.98 (dd, 1), 3.39 (1), 3.59 (dt, 1), 3.86 (dd, 1) 4.53 (dd, 1) 7.16-7.40 (m, 10); $^{13}$C NMR ($CDCl_3$) δ15.5 (q), 45.5 (t), 50.0 (t), 62.0 (t), 62.2 (t), 64.9 (d), 102.0 (d), 126.5, 127.3, 128.5, 129.5 (all d), 139.0, 143.8 (all s).

B. Synthesis of IDDC and the hydrochloride salt thereof

To a stirred solution of the acetal obtained above (2.16 g, 6.90 mmol) in $CDCl_3$ (5 ml) at 25° C. was added dropwise trifluoromethane-sulfonic acid (4.0 g, 36 mmol, Aldrich Co.). NMR spectroscopy indicated that the reaction was complete after 54 h. The black solution was diluted with water (50 ml), made basic with 1 N NaOH (200 ml), and extracted with $CH_2C_{12}$. The extract was concentrated to dryness and the residue was purified by flash chromatography over silica gel. Elution with 10:1 ether-THF gave first a small amount of 1,2-diphenylethylamine followed by a colorless fraction which was distilled at 170° C./0 5 mm to give an oily product (1.15 g, 75%) which solidified upon standing mp 79°-81° C. (lit.mp 74°-78° C; Dobson, T. A., *Chem. Abstr.* 73:3816 (1970), U.S. Pat. No. 3,509,158 (1970); lit m.p. 79° C., Takai, H. et al., *Chem. Pharm. Bull.* 34:1901 (1986)); $^1$H NMR ($CDCl_3$) δ 2.18 (bs, 1, NH), 3.23 (dd, 1, J=17.5 and 3.2, H-11), 3.33 (dd, 1, J=11.3 and 4.7, H-12), 3.50 (dd, 1, J=17.5 and 3.7, H11), 3.67 (d, 1, J=11.3, H-12), 3.92 (d, I, J=4.7, H-5), 4.33 (dd, 1 J=3.7 and 3.2, H-ID), 7.04-7.38 (m, 8H-1-4; 6-9); 13C NMR (CDC13) 41.8 (t), 47.0 (d), 50.8 (t), 55.1 (d), 125.1, 125.6, 126.1, 126.8, 126.9, 127.3, 128.1, 131.5 (all d), 135.4, 140.5, 141.6, 143.1 (all s); MS m/e 221 (40, M+), 220 (35), 192 (100), 191 (47).

HCl gas was bubbled into a solution of the product (700 mg) in ether (10 ml) and MeOH (10 ml) at 25-30° C. until no more precipitate formed. The solvent was removed and the residue was dissolved in hot EtOH and than allowed to cool, giving the hydrochloride salt of IDDC (429 mg, 52%) as white crystals: mp 305-307° C. (lit. mp. >270.C, see Dobson, T. A. et al; U.S. Pat. No. 3,509,158 (1970): *Chem. Abstr.* 73:3816 (1970)); $^1$H NMR ($CD_3OD$) δ 3.31 (dd, 1), 3.54 (dd, 1), 3.78 (dd, 1), 3.85 (d, 1), 4.25 (d, 1) 5.01 (t, 1), 7.07-7.46 (m 8): $^{13}$C NMR ($CD_3OD$) δ 36.5 (t), 43.5 (d), 48.3 (t), 54.9 (d), 125.7, 126.6, 126.8, 127.7, 127.9, 128.1, 129.5, 130.9 (all d), 132.0, 132.1, 140.0, 140.3 (all s).

Example 2: Synthesis of 5-Methyl-IDDC

A. N-Propargyl-1,2-diphenylethylamine

To a stirred solution of 1,2-diphenylethylamine (930 mg, 4.20 mmol) in EtOH (30 ml) were added 3-bromo-1-propyne (700 mg, 5.30 mmol) and potassium carbonate (1.38 g, 10. 0 mmol). The mixture was refluxed for 16 h and then more 3-bromo-1-propyne (100 mg) was added The mixture was refluxed another 6 h and then it was cooled, diluted with 1 N NaOH (200 ml) and extracted with $CH_2Cl_2$. The extract was dried ($MgSO_4$) and concentrated. The residue was purified by flash chromatography. Elution with 1:1 hexanes-$CH_2Cl_2$ gave first N,N-di-propargyl-1,2-diphenylethylamine (218 mg, 19%) [$^1$H NMR ($CDCl_3$) δ 2.34 (t,2), 2.83 (dd, 1), 3.53 (dd, 1), 3.63 (dd, 2), 3.71 (dd, 2), 3.85 (dd, 1), 6.89-6.92 (m, 2), 7.14-7.26 (m, 8); $^{13}$C NMR ($CDCl_3$)δ 40.5 (t), 40.9 (t), 68.2 (d), 73.4 (d), 79.4 (d), 126.1, 127.6, 128.1, 128.3, 128.8, 129.7, 129.8 (all d), 138.8, 140.8 (all s)]followed by N-propargyl-1,2-diphenylethylamine. Distillation at 180° C./0.5 mm gave the pure compound (583 mg, 59%) as a colorless oil: $^1$H NMR ($CDCl_3$) δ 1.69 (bs, 1), 2.20 (t, 1), 2.95 (dd, 1), 3.06 (dd, 1), 3.24 (dd, 1), 3.36 (dd, 1), 4.21 (dd, 1), 7.25-7.50 (m, 10); $^{13}$C NMR ($CDCl_3$) δ 36.0 (t), 45.1 (t), 62.6 (d), 71.6 (d), 82.2 (s), 126.7, 127.6, 127.8, 128.7, 129.5 (all d), 138.6, 142.7 (all s).

8 5-Methyl-IDDC

A solution of N-propargyl-1,2-diphenylethylamine (125 mg, 0.530 mmol) in chloroform (0.5 ml) and trifluoromethanesulfonic acid (500 mg, 3.33 mmol) was stirred for 48 h at 25° C. NMR spectral analysis of an aliquot revealed that only about a 40% conversion had taken place Therefore, additional trifluoromethanesulfonic acid (500 mg) was added. After 24 h, the black solution was made basic with 1 N NaOH (50 ml) and extracted with $CH_2Cl_2$. The solvent was evaporated and the residue was distilled to give the product (96 mg, 78%) as a colorless oil, bp 190-200° C./0 5 mm. $^1$H NMR ($CDCl_3$) δ 1.88 (s, 3), 2.44 (s, 1), 3.09 (d, 1), 3.32 (dd, 1), 3.59 (d, 1), 3.61 (dd, 1), 4.35 (dd, 1), 7.07-7.42 (m, 8); $^{13}$C NMR ($CDCl_3$) δ 22.6 (q), 41.9 (t), 55.5 (d), 58.1 (t), 62.6 (s), 122.9, 123.9, 125.0, 125.7, 126.4, 126.6, 127.3, 131.7 (all d), 136.3, 140.6, 144.3, 145.5 (all s).

Example 3 — Preparation of (+)-IDDC

A. Resolution of (±)-1,2-diphenylethylamine

The general procedure of V. M. Potapov et al. was adapted for the following resolution (Potapov, V. M. et al., *J. Oro Chem USSR* 16: 683 (1980)). To a stirred solution at 45° C. of 9.5013 grams (63.2 mmoles) of L-(+)-tartaric acid (Mallinkrodt, used as received) in 400 mL of water was added dropwise, 24.7673 grams (125.5 mmoles) of (±)-1,2-diphenylethylamine (Aldrich, used as received). A white precipitate formed immediately. After stirring for 2.5 hours at 25° C. the precipitate was collected and partially air dried to yield 94 grams of white solid. These 94 grams were dissolved in 300 mL of boiling water then filtered while hot to give a clear, colorless solution. Crystallization commenced from this solution within 20 min. The collected crystals amounted to 31.6 grams after partial air drying Subsequently, five more recrystallizations were performed on this material using proportional amounts of boiling water to give 905.2 mg of the partially resolved diastereoisomeric salt of (+)-L-tartaric acid and (+)-1(R),2-diphenylethylamine as white microcrystals; mp 222.5°-223.5° C. dec, $[\alpha]_D^{19} = -51.3°$, C.=.92, $H_2O$. Nakazaki et al., *Bull Chem. Soc. Jpn.* 36:161 (1963) report the following physical constants. (+)-tartrate of (−)-1(R),2-diphenylethylamine MP 229°×230° C., $[\alpha]_D^{19} = -55.3°$, C=92, $H_2O$; (−)-1(R),2-diphenylethylamine $[\alpha]_D^{19} = -51.2°$, C=3.7, EtOH. The mother liquors from the last four recrystallizations were combined. The aqueous solution was concentrated, made basic by the addition of solid NaOH and extracted with three portions of $CH_2Cl_2$. The combined organic layers after drying ($K_2CO_3$) and removal of the solvent in vacuo yielded 2.5397 grams of partially resolved (−)-1(R),2-diphenylethylamine; $[\alpha]_D^{19} = -44.0°$ C., C=3.7, EtOH (Nakazaki, M., et al.: supra) The amine (2.5055 grams, 12.7 mmoles) was added dropwise to a stirred solution at 45° of 1.8116 grams (12.1 mmoles) of L-(+)-tartaric acid (Mallinkrodt, used as received) in 40 mL of water. The resulting white precipitate was collected after the mixture had stirred at ambient temperature for 12 hours. The collected solid was recrystallized three times from boiling $H_2O$ to yield 815.2 mg of the diastereo-isomeric salt of (+)-L-tartaric acid and (−)-1(R),2-diphenylethylamine as white microcrystals; mp 224°-225° C. dec, $[\alpha]_D^{19} = -54.8°$, C=.92, $H_2O$. Nakazaki et al , supra The salt (806.6 mg) was dissolved in 50 mL of 1N NaOH and 25 mL of $CH_2Cl_2$. The layers were separated and the aqueous portion was extracted with 2×25 mL of $CH_2Cl_2$. The combined organic layers were washed with 15 ml of 1N NaOH, dried ($K_2CO_3$), and the solvent removed at reduced pressure to give 449.1 mg of (−)-1(R),2-diphenylethylamine as a colorless liquid; $[\alpha]_D^{19} = -50.1°$, C=3.7, EtOH.

B Preparation of N-(1(R),2-diphenylethyl)aminoacetaldehyde diethyl acetal

The general procedure of Suzuki, T., et al., *Chem. Pharm. Bull* 34; 1988 (1986), was adapted for the following alkylation. To a stirred mixture at 90° C. of 249.5 mg (1.3 mmoles) of (−)-1(R),2diphenylethylamine and 193.6 mg (1.4 mmoles) of anhydrous potassium carbonate (Baker, used as received) in 2.5 ml of N,N-dimethylformamide (Baker, used as received) was added dropwise, over two hours, a solution of 284.1 mg (1.4 mmoles) of bromoacetaldehyde diethylacetal (Aldrich, distilled, bp 83° C./ 40mm) The resulting mixture was heated (95°-105° C.) with stirring. After 16 hours the reaction mixture was cooled to 10° C., 50 mL of 1N NaOH was added followed by 25 mL of $CH_2Cl_2$. The layers were separated and the aqueous layer was extracted with 2×15 mL of $CH_2Cl_2$. The combined organic layers were washed with 10 mL of 1N NaOH, dried ($K_2CO_3$) and the solvent evaporated at reduced pressure to give 346.1 mg of brown oil. The oil was distilled (180°-190° C., 0.05 mm/Hg) using a Kugelrohr apparatus to give 315.5 mg of light yellow oil. The yellow oil (304.2 mg) was chromatographed (10 g silica gel) using 25 mL $Et_2O$ followed by 40 mL 3:1 $Et_2O/THF$ then 40 mL 2:1 $Et_2O/THF$ as eluent The fractions containing the less polar material (Rf .56) were combined and the solvent removed at reduced pressure yielding 283.3 mg of N-(1(R),2-diphenylethyl)aminoacetaldehyde diethyl acetal as a clear, light yellow liquid (71% yield). $^1H$ NMR ($CDCl_3$): δ 1.09 and 1.11 (t, 6H, J=6.9, $-CH_3$), 1.76 (bs, 1H, NH), 2.51 (dd, 1H, J=12.0 and 6.3, $-CH_2-N$), 2.57 (dd, 1H, J=12.0 and 5.0, $-CH_2-N$), 2.91 (dd, 1H, J=13.2 and 8.5, $CH_2$-Phenyl), 2.98 (dd, 1H, J=13.2 and 5.9, $-CH_2$-Phenyl), 3.37 and 3.43 (dt, 2H, J=9.3 and 7.2, $-CH_2$), 3.53 and 3.57 (dt, 2H, J=9.3 and 6.9, $-CH2-0$), 3.86 (dd, 1H, J=8.5 and 5.9, $-CH-N$), 4.53 (dd, 1H, J=6.3 and 5.0, $-CH-0$), 7.16-7.34 (m, 1OH, Phenyl).

C. Preparation of (+)-10,5-(Iminomethano)-10,11-dihydro-5H-dibenzoa[a,d]cycloheptene (IDDC) cycloheptene (IDDC)

The general procedure of T. Suzuki et al; suora. was adapted for the following cyclization To 6 ml of perchloric acid (70% aqueous) at 24°]C. was added dropwise with stirring over 5 min. 280 mg (8.9 mmoles) of N-(1(R),2-diphenylethyl)aminoacetaldehyde diethyl acetal During the addition a brown oil separated. The mixture was stirred for 16 hours at ambient temperature then poured onto 50 mL of 2N NaOH and extracted with 3×15 mL of $CH_2Cl_2$. The combined organic layers were washed with 15 mL of 1N NaOH, dried ($K_2CO_3$) and the solvent removed at reduced pressure to give 225.4 mg of brown oil. A TLC (THF) showed two spots with Rf values of 0.67 and 0.23. The oil (225 mg) was submitted to flash chromatography (8 grams silica gel) eluting with 25 mL of $Et_2O$, 40 mL 3:1 $Et_2O/THF$, 25 mL 2:1 $Et_2O/THF$, 25 mL 1:1 A82–02.WP $Et_2O/THF$, and 25 mL THF. The fractions containing the more polar material (Rf .22) were combined and the solvent evaporated in vacuo to give 172.1 mg of brown oil. This oil was double distilled (175°-185° C., 0.05 mm/Hg) using a Kugelrohr apparatus to give 153.4 mg of (+)-IDDC as a clear light yellow oil that solidified on standing (mp 79°-85° C., $[\alpha]_D^{25} = +161.5°$, C.=1, EtOH) (78% yield) $^1H$ NMR ($CDCl_3$): δ 2.10 (bs, 1H, -NH), 3.23 (dd, 1H, J=17.5 and 3.2, H-11), 3.33 (dd, 1H, J=11.1 and 4.6, H-12), 3.51 (dd, 1H, J=17.5 and 3.7, H-11), 3.67 (d, 1H, J=11.1, H-12), 3.93 (d, 1H, J=4.2, H-5), 4.34 (t, 1H, J=3.6, H-10), 7.05-7.30 (m, 8H, H-1,2,3,4,6,7,8,9). 13C NMR (CDC13): 41.7 (t, C-11), 46.9 (d, C-5), 50.8 (t, C-12), 55.1 (d, C-10), 125.0, 125.6, 126.0, 126.8, 126.9, 127.3, 128.0, 131.5 (d, C-1,2,3,4,6,7,8,9) 135.4, 140.4, 141.6, 143.0 (s, C-4a,5a, 9a, 11a).

Preparation of the Maleate Salt of (+)-IDDC

To a stirred solution at 43° C. of 50.6 mg (.23 mmoles) of (+)-IDDC in 1.0 ml of EtOH was added a solution of 26.4 mg (.23 mmoles) of maleic acid (Aldrich, used as received) in 0.3 ml of EtOH. Crystallization begins from the resulting solution in approximately 10 minutes. This mixture was then stirred at ambient temperature. After 14 hours, the white crystals were collected and then recrystallized from 0.4 ml of hot EtOH to give 31.1 mg of the maleate salt of (+)IDDC (mp 168°-168.5° C. dec). From the mother liquors were isolated, after recrystallization, two subsequent portions of the maleate salt of 10.2 mg (mp 167°-167.5° C. dec) and 13.8 mg (mp 164°-165.6.C dec).

Example 4—Preparation of Optically Active N-MethYl-IDDC

To a stirred solution of (+)-IDDC (9.3 mg, 0.04 mol; $[\alpha]_D^{25} = +116.3°$, EtOH, c=1) in acetonitrile (0.4 ml) and 37% aqueous formaldehyde (0.61 mmol) at 25° C. was added sodium cyanoborohydride (5.1 mg, 0.08 mmol). The resulting mixture was stirred for 15 min. and then one drop of glacial acetic acid was added to lower the pH to 7 (checked by wet pH paper). The mixture was stirred for 20 h and the solvent was removed in vacuo. The residue was treated with 2 N sodium hydroxide (4 ml) and ether (4 ml). The layers were separated and the aqueous layer was extracted with ether. The combined organic layers were dried ($K_2CO_3$), filtered, and evaporated to give a clear oil (11 mg) which was purified by preparative TLC on silica gel. Elution with ethanol gave two bands, $R_f=0.41$ and 0.83. The band at 0.41 was removed and extracted with acetone. The solution was dried ($K_2CO_3$) and evaporated to give optically active N-methyl IDDC (10.6 mg, 84%) as an off-white oil; $^1$H NMR ($CDCl_3$) $\delta$ 2.50 (s, 3, N-Me), 2.92 (dd, 1, J=10.5 and 4.8, H-12), 3.00 (dd, 1, J=17.7 and 3.3, H-11), 3.58 (dd, 1, J=10.5 and 1.1, H-12), 3.62 (dd, 1, J=17.7 and 3.9, H-11), 3.83 (dd, 1, J=4.7 and 1.1, H-5), 3.94 (dd, 1, J=3.9 and 3.0, H-10). $^{13}$C NMR ($CDCl_3$) $\delta$ 38.61 (t), 45.2 (q), 47.0 (d), 59.8 (t), 62.7 (d), 125.1, 125.9, 126.0, 126.7, 127.3, 127.8, 131.3 (all d), 135.2, 138.6, 141.4, 142.5 (all s).

Example 5—The PCP Receptor Bindinq Properties of the IDDC Optical Isomers

The PCP receptor binding properties of various compounds of the invention against $^3$H-5-methyl-10,11-dihydro-5H-dibenzoa,d]cyclohept-ene-5,10-imine (3H-MK-801) were deterimed. The results appear in Table 1, below.

TABLE 1

| Compound | $IC_{50}$ [± sem(n)] $^3$H-MK-801 (nanomolar) |
|---|---|
| (±)-IDDC | 41 ± 6 (5) |
| (+)-IDDC | 40 ± 5 (4) |
| (+) N-Methyl-IDDC | 65 ± 9 (3) |
| (±) 5-Methyl-IDDC | 125 (1) |

Example 6 Electrophysiological Assays (+)-IDDC was tested for its ability to achieve use-dependent blockage of NMDA-induced (+glycine) responses on rat hippocampal neurons maintained in cell culture. This compound produced a result very similar to the use dependent blocking action exhibited by MK-801.

Hippocampal neurons were obtained from the CA1 region of the hippocampus from 1-3 day-old-newborn rats (Long-Evans). Small blocks of tissue (>1mm$^3$) were incubated in papain (20 units ml$^{-1}$; Worthington-Cooper) for 30 minutes The tissue was dissociated into a single cell suspension by trituration with a fire-polished Pasteur pipette in complete growth medium (Earle's MEM, 20 mM glucose, 50 units/ml penicillin/streptomycin, 5% heat-inactivated fetal calf serum, Serum Extender from Collaborative Research) containing 2.5 mg/ml bovine serum albumin and 2.5 mg/ml trypsin inhibitor (Sigma) The cells were plated onto glass coverslips coated with collagen/poly-D-lysine. Cultures were fed every 3 days by replacing half the volume of medium. Arabinosylcytosine (5×10$^6$M) was added to the cultures for 1 or 2 days during the first week after plating to suppress the proliferation of non-neuronal cells.

All electrophysiology experiments were performed with the wholecell mode of patch clamp recording [Hamill, O. D., Marty, A., Neher, E., Sakman, B., and Sigworth, F. J., Pflugers Arch. 391, 85–100 (1981)]from neurons grown for 1-3 weeks in culture. Agonists and agonist/antagonist combinations were applied by a U-tube tool (Fenwick et al; J. Physiol. 331:577–597 (1982)) to neurons in whole-cell experiments. The external solution contained (in mM) NaCl 140, KCl 3.5, CaCl$_2$ 1, glucose 5, picrotoxinin 0.02, tetrodotoxin (TTX) 5×10$^{-4}$, and N-2- hydroxyethylpiperazine-N'-2-ethanesulfonic acid (HEPES) 10. The pH of this solution was adjusted to 7.4 with NaOH. The internal (patch electrode) solution contained (mM) Cs-methanesulfonate 120, CsCl 10, ethyleneglycol-bis-($\beta$-aminoethylether)-N,N,N',N'-tetraacetic acid (EGTA) 10, HEPES 10 (pH adjusted to 7.0 with CsOH). Membrane current was filtered at 4000 Hz (−3dB; 8-pole Bessel) and recorded on magnetic tape for later analysis Experiments were performed at room temperature (20°-25° C.) Sources of chemicals: N-methyl-D-aspartate, Cambridge Research Biochemicals; pirotoxinin, Sigma Chemical Company; salts for recording solutions, Aldrich (Gold Label) or Alfa H (Puratronic). [$^3$H]Kainate and $^3$H]CPP and [$^3$H]AMPA were purchased from Dupont/NEN (Boston, Mass.)].

Three second applications of 50 uM NMDA in the presence of 1 uM glycine resulted in inward whole-cell currents of 100–1000 pA at a holding potential of −60 mV. Repetitive applications (every 30 s) to the same cell produced currents which varied less than 5% over a period of at least 30 minutes. When MK-801 (10 uM) was applied in conjunction with NMDA, the inward current became progressively smaller with serial applications Recovery from this inhibition required repeated applications of NMDA alone and was speeded by holding the membrane potential at positive voltages.

Identical to MK-801, (+) N-methyl IDDC (10 uM) inhibited the NMDA current in a use-dependent and voltage-dependent manner. Serial applications evoked progressively smaller currents Inhibition by (+) N-methyl IDDC was reversed only with prolonged or repeated application of NMDA. The rate of recovery from blockade by (+) N-methyl IDDC was somewhat more rapid than the rate of recovery of responses following MK-801. This observation is consistent with the observation that (+) N-methyl IDDC has a lower affinity than MK-801 for the PCP receptor

Example 7. In Vitro Neurotoxicity Assay

Dissociated rat hippocampal cultures were prepared using a modification of the method of Huettner and Baughman Huettner, J. E. and Baugham, R. W., J. Neurosci 6, 3044–3060 (1986)]. The cortices were removed from 1-3 day post-natal rats (Sprague-Dawley) that had been anesthetized with chloral hydrate, and the hippocampi were dissected out and placed in Cl- free dissociation medium supplemented with 1 mM kynurenic acid and 10 mM MgSO$_4$ (Choi, D. W., J. Neurosci. 7, 369–379 (1987)). The hippocampi were washed in the dissociation medium, then incubated for 2×20 minutes at 37° C. in dissociation medium containing 10 units/ml of Papain (Worthington). After the enzyme treatment, the tissue was incubated for three 5-minute periods at 37° C. with 10 mg/ml trypsin inhibitor (Sigma type II-0)

The cells were dissociated by trituration in growth medium and plated as 0.15 ml droplets of cell suspension onto the center of 35 mm Primaria (Falcon) dishes that had been stamped with a labeled 26×26 grid of approximately 0.64 cm$^2$ total area using a Mecanex BB form (WPI, New Haven, Conn.) and coated with poly-D-lysine and laminin (Collaborative Research). The cell density was between 2.5 and 4.0×10$^5$ cells per dish. The growth medium was Eagles minimum essential media (MEM, Earle's salts) supplemented with 5% fetal bovine serum (CCL), 5% defined supplemented calf serum (HyClone), 50 mM glucose, 50 units/ml penicillin/streptomycin and MITO+serum extender (Collaborative Research). The cells were maintained at 37° C. in a humidified 4.5% $CO_2$ atmosphere. Cells were left for 12–14 hours to attach to the plate surface, then 1.5 mls of growth medium was added to each dish, 1 ml removed and replaced with a further 1 ml of fresh medium. This process removed most of the cell debris and unattached cells. The area of cell attachment and proliferation did not significantly extend beyond the treated central area. After 2–4 days in culture, nonneuronal cell division was arrested by a 2–3 day exposure to 5 uM cytosine arabinoside.

The cells were maintained in a medium that was similar to the growth medium but without the fetal bovine serum. The medium was changed on a weekly schedule, replacing two-thirds the volume with fresh medium. The only glutamate present in the media was that contained in the calf serum which gave a final concentration of 12 uM.

Before treatment, sister cultures were examined under phasecontrast microscopy to ensure that the cultures were of a similar density. Exposure to glutamate was carried out at 32°–34° C. in a HEPES-buffered 'control salt solution' (CSS) similar to that reported in Choi, D. W., Maulicci-Gedde, M. and Viriegstein, A. R., *J. Neurosci.* 7, 257–268 (1987), but with 10 mM HEPES substituted for Tris-HCl and buffered for pH 7.4 at 34° C. The cultures were washed twice with CSS and then incubated for 5 minutes in CSS containing 1 uM glycine and the compound to be tested (the controls had 1 uM glycine only). Glycine was included since it has been shown to potentiate the effects of glutamate at the NMDA site [Johnson, J. W. and Ascher, P., *Nature* 325, 529–530 (1987)]and the preincubation with the test drugs enhances the neuroprotection activity (Finkbeiner, S.C., et al., *Proc. Natl. Acad. Sci. USA* 85:4071–4074 (1988)). CSS containing 1 uM glycine plus drug and a known concentration of glutamate (0–1000 uM) were added by triple exchange and the cultures were incubated for 5 minutes. The cultures were washed four times with CSS and then with medium before being placed in the incubator overnight. Cultures were removed from the incubator the next day, washed twice with CSS and treated for 5 minutes with 0.4% Trypan Blue, a dye that is only taken up by dead and dying cells. The cultures were washed three times and the surviving cells counted in the grid area using phase contrast microscopy. Cell survival was normalized as a percentage of the highest cell count, and the results plotted against glutamate concentration. Cultures not exposed to glutamate generally had between 4500 and 5500 surviving cells in the grid area.

Figure 1:
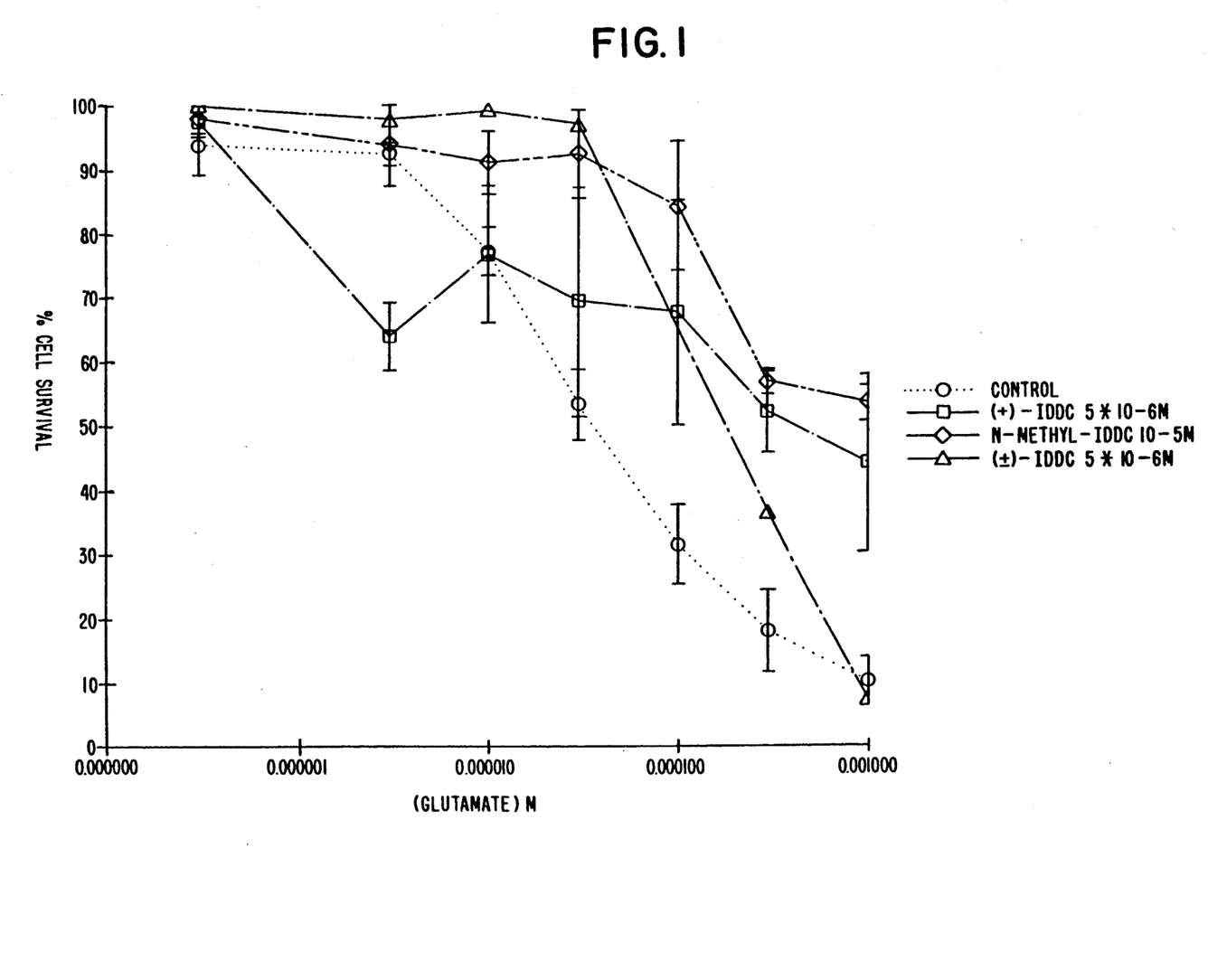
FIG. 1 depicts a graph showing the in vitro neuroprotective effect of (±) 10,5-(iminomethano)-10,11-dihydro-5H-dibenzoa,d]cycloheplene (IDDC), (+) IDDC, N-methyl IDDC and a control sample on rat hippocampal cells treated with various concentrations of glutamate.

(±)-IDDC was tested for its neuroprotective properties against a range of glutamate concentrations. FIG. 1 depicts a graph showing the in vitro neuroprotective effect of (±)-IDDC, (+)-IDDC, N-methyl IDDC and a control sample on rat hippocampal cells treated with various concentrations of glutamate. As illustrated in FIG. 1, cultures tested with 5 uM (±)-IDDC, 5 uM (+)-IDDC and 10 uM N-methyl IDDC exhibited enhanced cell survival when compared to control values

Example 8. In Vivo Neurotoxicity Assay

Figure 2:
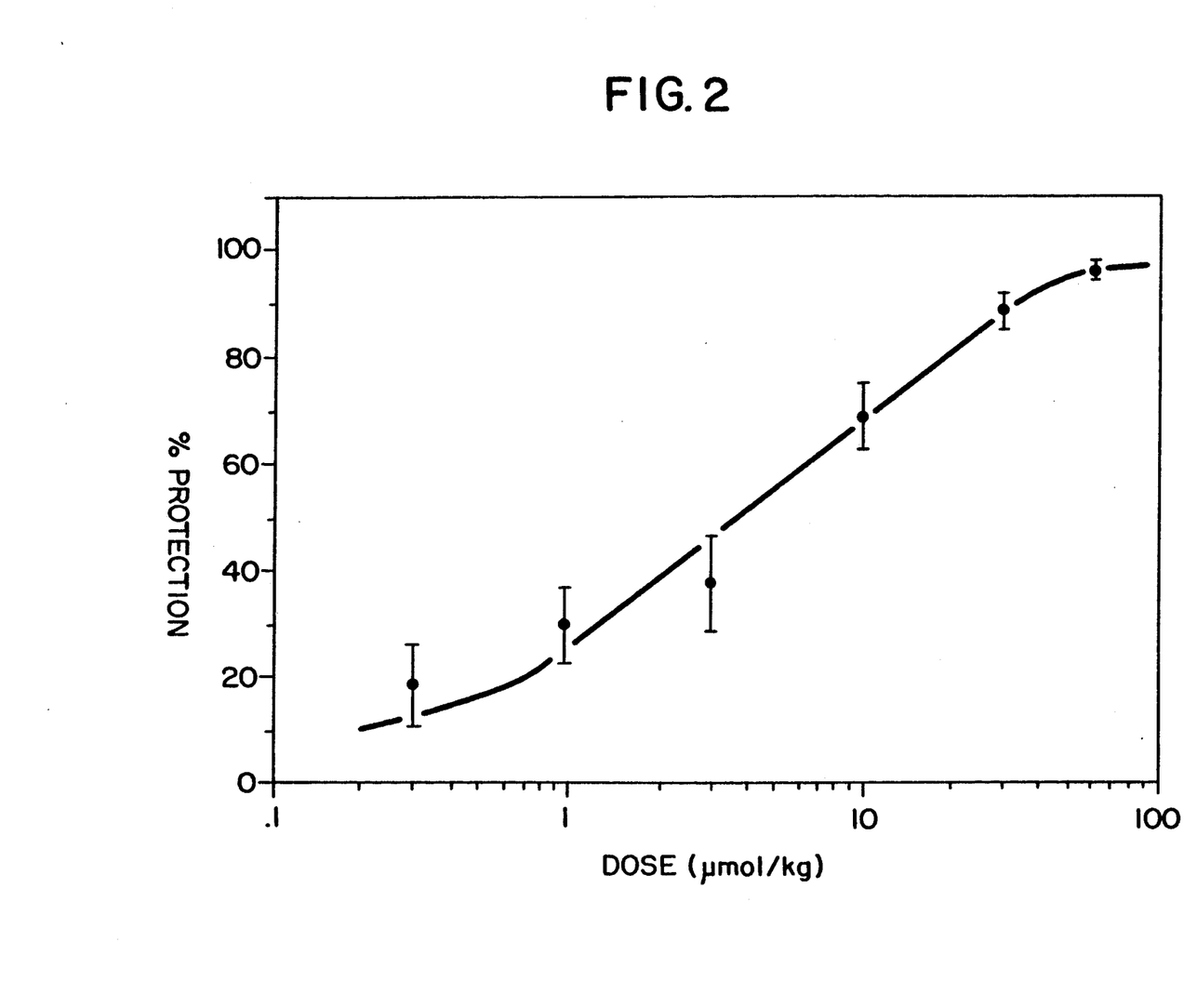
FIG. 2 depicts a graph showing the in vivo neurotoxicity protective effect of (+)-IDDC at various dosage levels.

The experimental model of McDonald, J. W., et al; supra. was employed with the single alteration in protocol of an intraperitoneal injection of the test compound 15 minutes following, rather than preceding, the cerebral NMDA injection. As shown in FIG. 2, (+)IDDC was found, in dosages ranging from about 0.30 to 60 μMol/kg of body weight, to protect against the lesions caused by NMDA injection.

These observations on the in vitro and in vivo neuroprotective properties of IDDC are consistent with its affinity for the PCP binding site in brain and the inhibition of the NMDA current described above.

Having now fully described this invention, it will be understood by those of skill in the art that the same can be performed within a wide and equivalent range of conditions, formulations and other parameters without affecting the scope of the invention or any embodiment thereof.

What is claimed is:

1. A method of treating or preventing neuronal loss, comprising administering to an animal in need of such treatment a compound of the formula:

wherein:

R is hydrogen, $C_2$–$C_6$ acyl, $C_1$–$C_6$ alkyl, aryl, $C_1$–$C_6$ alkoxycarbonyl, $C_7$–$C_{10}$ aralkyl, $C_2$–$C_6$ alkenyl, $C_3$–$C_{15}$ dialkylaminoalkyl, $C_1$–$C_6$ hydroxyalkyl, $C_2$–$C_6$ alkynyl, $C_3$–$C_{15}$ trialkylsilyl, $C_4$–$C_{10}$ alkylcycloalkyl, or $C_3$–$C_6$ cycloalkyl;

$R^1$ is hydrogen, $C_1$–$C_6$ alkyl, $C_2C_6$ alkenyl, $C_{7-C10}$ aralkyl, $C_1$–$C_6$ alkoxy or $C_3$–$C_{15}$ dialkylaminoalkyl;

X and Y are independently selected from the group consisting of chloro, fluoro, bromo, iodo, $C_1$–$C_6$ alkoxy, $C_2$–$C_6$-dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;

Z represents a group selected from $$\diagdown C=O \quad \diagdown C \diagup^H_H \quad , \diagdown C \diagup^{R^3}_H \quad , \diagdown C \diagup^{R^3}_{OH} \quad , \text{or} \diagdown C \diagup^H_{OR^2} \quad ;$$

wherein $R^2$ is hydrogen, $C_1$–$C_6$ alkyl, $C_2$–$C_6$ alkenyl, aralkyl, $C_4$–$C_{15}$ dialkylaminoalkyl, $C_2$–$C_6$ acyl, aroyl, or aralkanoyl, and $R^3$ is $C_1$–$C_6$ alkyl, $C_2$–$C_6$ alkenyl, phenyl, aralkyl or $C_3$–$C_{15}$ dialkylaminoalkyl; and n is an integer selected from 0 (X or Y is hydrogen, respectively), 1, 2, 3, or 4;

or a pharmaceutically acceptable salt thereof;

wherein said compound exhibits a high binding activity with respect to the PCP receptor in mammalian nerve cells, and wherein said compound is administered in an amount effective to treat or prevent said neuronal loss.

2. The method of claim 1, wherein said neuronal loss is associated with ischemia, hypoxia, hypoglycemia, or brain and spinal cord trauma, or treating Alzheimer's disease, amyotrophic lateral sclerosis, Huntington's disease, or Down's Syndrome.

3. The method of claim 1, wherein R is hydrogen.

4. The method of claim 1, wherein R and $R^1$ are hydrogen or methyl and n is 0.

5. The method of claim 1, wherein said compound has the formula:

6. The method of claim 1, wherein said compund has the formula:

7. The method of claim 1, wherein said compound has the formula:

8. The method of claim 1, wherein said compound has the formula:

9. The method of claim 1, wherein said animal is a human.

10. The method of claim 1, wherein said compound is administered as a pharmaceutical composition in admixture with a pharmaceutically acceptable carrier.

11. The merthod of claim 1, wherein said compound is administered orally.

12. The method of claim 1, wherein said animal is suffering from ischemic brain insult.

13. The method of claim 5, wherein said animal is a human suffering from ischemic brain insult, and said compound is administered as a pharmaceutical composition in admixture with a pharmaceutically acceptable carrier.

14. A method of inhibiting NMDA receptor-ion channel related neurotoxicity comprising administering to an animal in need of such treatment a pharmaceutical composition comprising a compound of the formula:

wherein:

R is hydrogen, $C_2$–$C_6$ acyl, $C_1$–$C_6$ alkyl, aryl, $C_1$–$C_6$ alkoxycarbonyl, $C_7$–$C_{10}$ aralkyl, $C_2$–$C_6$ alkenyl, $C_3$–$C_{15}$ dialkylaminoalkyl, $C_1$–$C_6$ hydroxyalkyl, $C_2$–$C_6$ alkynyl, $C_3$–$C_{15}$ trialkylsilyl, $C_4$–$C_{10}$ alkylcycloalkyl, or $C_3$–$C_6$ cycloalkyl;

$R^1$ is hydrogen, $C_1$–$C_6$ alkyl, $C_2$–$C_6$ alkenyl, $C_7$–$C_{10}$ aralkyl, $C_1$–$C_6$ alkoxy or $C_3$–$C_{15}$ dialkylaminoalkyl;

X and Y are independently selected from the group consisting of chloro, fluoro, bromo, iodo, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1C_6$ N-alkylcarbamoyl, $C_2$–$C_{15}$ N,N-dialkylcarbamoyl, nitro and $C_2$–$C_{145}$ dialkylsulfamoyl;

Z represents a group selected from $$\diagdown C=O \quad \diagdown C \diagup^H_H \quad , \diagdown C \diagup^{R^3}_H \quad , \diagdown C \diagup^{R^3}_{OH} \quad , \text{or} \diagdown C \diagup^H_{OR^2} \quad ;$$

wherein $R^2$ is hydrogen, $C_1$–$C_6$ alkyl, $C_2$–$C_6$ alkenyl, aralkyl, $C_4$–$C_{15}$ dialkylaminoalkyl, $C_2$–$C_6$ acyl, aroyl, or aralkanoyl, and $R^3$ is $C_1$–$C_6$ alkyl, $C_2$–$C_6$ alkenyl, phenyl, aralkyl or $C_3$–$C_{15}$ dialkylaminoalkyl; and n is an integer selected from 0 (X or Y hydrogen, respectively), 1, 2, 3, and 4, or a pharmaceutically acceptable salt thereof; and a pharmaceutically acceptable carrier;

wherein said compound exhibits a high binding activity with respect to the PCP receptor in mammalian nerve cells, and wherein said compound is present in an amount effective to inhibit the neurotoxicity.

15. The method of claim 14, wherein R is hydrogen.

16. The method of claim 14, wherein R and $R^1$ are hydrogen or methyl and n is 0.

17. The method of claim 14, wherein said compound has the formula:

18. The method of claim 14, wherein said compound has the formula:

19. The method of claim 14, wherein said compound has the formula:

20. The method of claim 14, wherein said compound has the formula:

21. The method of claim 14, wherein said neurotoxicity is caused by excessive release of endogenous glutamate following ischemic brain insult.

22. The method of claim 14, wherein said animal is a human.

23. The method of claim 14, wherein said compound is administered as a pharmaceutical composition in admixture with a pharmaceutically acceptable carrier.

24. The method of claim 14, wherein said compound is administered orally.

25. The method of claim 14, wherein said animal is suffering from ischemic brain insult.

26. The method of claim 17, wherein said animal is a human suffering from ischemic brain insult, and said compound is administered as a pharmaceutical composition in admixture with a pharmaceutically acceptable carrier.

* * * * *

UNITED STATES PATENT AND TRADEMARK OFFICE
CERTIFICATE OF CORRECTION

PATENT NO. : 5,011,834
DATED : April 30, 1991
INVENTOR(S) : Weber et al.

It is certified that error appears in the above-identified patent and that said Letters Patent is hereby corrected as shown below:

Column 1, immediately before "FIELD OF THE INVENTION" please insert the following text, on line 4:

--STATEMENT AS TO RIGHTS TO INVENTIONS MADE UNDER FEDERALLY SPONSORED RESEARCH AND DEVELOPMENT

This invention was made with government support under Grant Nos. MH 40303 and MH 42068 awarded by the National Institutes of Health. The government has certain rights in the invention.--

Signed and Sealed this

Ninth Day of February, 1993

Attest:

STEPHEN G. KUNIN

*Attesting Officer*     Acting Commissioner of Patents and Trademarks